(12) United States Patent
Miyakawa et al.

(10) Patent No.: US 9,353,151 B2
(45) Date of Patent: May 31, 2016

(54) HLA-BINDING PEPTIDE, AND DNA FRAGMENT AND RECOMBINANT VECTOR CODING FOR SAID HLA-BINDING PEPTIDE

(71) Applicants: NEC Corporation, Tokyo (JP); KOCHI UNIVERSITY, Kochi-shi (JP)

(72) Inventors: Tomoya Miyakawa, Tokyo (JP); Keiko Udaka, Nankoku (JP)

(73) Assignees: NEC CORPORATION, Tokyo (JP); KOCHI UNIVERSITY, Kochi (JP)

( * ) Notice: Subject to any disclaimer, the term of this patent is extended or adjusted under 35 U.S.C. 154(b) by 86 days.

(21) Appl. No.: 13/833,014

(22) Filed: Mar. 15, 2013

(65) Prior Publication Data

US 2014/0094586 A1 Apr. 3, 2014

Related U.S. Application Data

(62) Division of application No. 11/814,709, filed as application No. PCT/JP2005/022365 on Dec. 6, 2005, now Pat. No. 8,487,076.

(30) Foreign Application Priority Data

Jan. 25, 2005 (JP) ................................. 2005-017140

(51) Int. Cl.
*A61K 38/04* (2006.01)
*C07K 7/06* (2006.01)
*C07K 14/47* (2006.01)
*A61K 38/00* (2006.01)

(52) U.S. Cl.
CPC ............... *C07K 7/06* (2013.01); *C07K 14/4738* (2013.01); *A61K 38/00* (2013.01)

(58) Field of Classification Search
None
See application file for complete search history.

(56) References Cited

U.S. PATENT DOCUMENTS

| 7,342,093 | B2 * | 3/2008 | Altieri et al. | .................. | 530/324 |
| 8,324,345 | B2 | 12/2012 | Miyakawa et al. | | |
| 2004/0180354 | A1 * | 9/2004 | Simard et al. | .................... | 435/6 |

| 2004/0210035 | A1 | 10/2004 | Straten et al. |
| 2008/0044484 | A1 | 2/2008 | Minev |
| 2008/0206270 | A1 | 8/2008 | Minev |

FOREIGN PATENT DOCUMENTS

| JP | 08151396 | 6/1996 |
| JP | 2002-284797 | 10/2002 |
| WO | 2004067023 | 8/2004 |
| WO | 2006/014579 | 2/2006 |

OTHER PUBLICATIONS

European Search Report, Application No. 05814549.1, dated Jul. 11, 2008.
Japanese Patent Office issued a Japanese Office Action dated Apr. 21, 2009, Application No. 2006-520609.
Hirohashi, Y. et al.: "An HLA-A24-restricted Cytotoxic T Lymphocyte Epitope of a Tumor-associated Protein, Survivin", Clinical Cancer Research, The American Association for Cancer Research, U.S., vol. 8, No. 6, Jun. 1, 2002, pp. 1731-1739, XP002283856, ISSN: 1078-0432.
Partial European Search Report issued on Dec. 2, 2011 by the European Patent Office in corresponding European Patent Application No. 10192727.5, 8 pages.
Extended European Search Report dated May 15, 2012, with English translation; Application No. 10192727.5.
Sine Reker et al.: "Identification of Novel Survivin-Derived CTL Epitopes", Cancer Biology and Therapy, Landes Bioscience, US, vol. 3, No. 2, Feb. 1, 2004, pp. 173-179, XP008066706.
Publication of the European Search Report dated Jun. 18, 2012, with English translation; Application No. 10192727.5.

* cited by examiner

*Primary Examiner* — Michael Burkhart
(74) *Attorney, Agent, or Firm* — Young & Thompson

(57) ABSTRACT

An HLA-binding peptide binding to a HLA-A type molecule, the HLA-binding peptide includes at least one type of amino acid sequence selected from the group consisting of SEQ ID NOS: 1 to 80, and consists of not less than 8 and not more than 11 amino acid residues. All of these amino acid sequences herein mentioned are the predicted amino acid sequences binding to a human HLA-A type molecule with the prediction program using the certain active learning method.

4 Claims, 1 Drawing Sheet

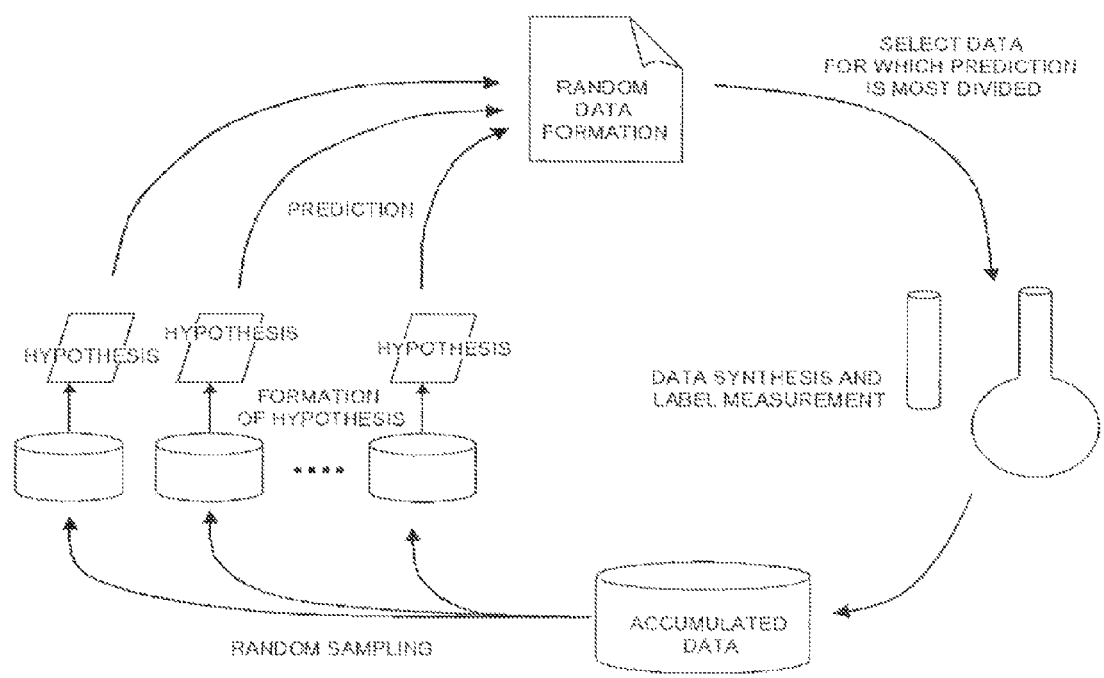

HLA-BINDING PEPTIDE, AND DNA FRAGMENT AND RECOMBINANT VECTOR CODING FOR SAID HLA-BINDING PEPTIDE

TECHNICAL FIELD

The present invention relates to an HLA-binding peptide, and to a DNA fragment and a recombinant vector coding for the HLA-binding peptide.

BACKGROUND ART

When a cancer antigen that is specific to a cancer cell is present on the surface of the cancer cell, there are times when an innate immune reaction as a result of the cancer cell being recognized as a substance foreign to oneself proceeds, and a specific immune response is subsequently induced to thus cause a reaction to eliminate the cancer cell.

When a specific immune response is induced, cancer cell-derived fragments and the like in body fluids are eliminated by neutralizing antibodies, and the cancer cells themselves are eliminated by cytotoxic T lymphocytes (CTLs). That is, the CTL specifically recognizes a cancer antigen (CTL epitope) consisting of 8 to 11 amino acids presented in an HLA class I molecule on the surface of a cancer cell, and eliminates the cancer by damaging the cancer cell. Therefore, it is critical to identify such a cancer-specific CTL epitope in order to develop a therapeutic vaccine for the cancer.

A technique of this kind is known from Patent Publication 1. Patent Publication 1 states that an oligopeptide formed from a specific amino acid sequence has the property of binding to an HLA.
[Patent Publication 1] Japanese Patent Application Laid-open No. H8-151396 (1996)

DISCLOSURE OF THE INVENTION

However, the conventional technique described in the above-mentioned publication has room for improvement with regard to the following points.

Firstly, it is unclear whether or not the HLA-binding peptide of the above-mentioned publication binds to an HLA molecule effectively, and there is still room for improvement in terms of the HLA-binding properties.

Secondly, it is stated that the HLA-binding peptide of the above-mentioned publication has the property of binding to HLA-DQ4. However, it is unclear whether or not it binds to an HLA-A2 molecule (product of the HLA-A*0201 gene and the like), which is often seen in European and American people, and an HLA-A24 molecule (product of the HLA-A*2402 gene and the like), which is often seen in Japanese people.

The present invention has been accomplished under the above-mentioned circumstances, and it is an object thereof to provide an HLA-binding peptide that exhibits high-affinity binding to a specific type of HLA molecule.

According to the present invention, there is provided an HLA-binding peptide binding to a HLA-A type molecule, the HLA-binding peptide comprising at least one type of amino acid sequence selected from the group consisting of SEQ ID NOS: 1 to 80, and consisting of not less than 8 and not more than 11 amino acid residues.

Furthermore, according to the present invention, there is provided the HLA-binding peptide, comprising at least one type of amino acid sequence selected from the group consisting of SEQ ID NOS: 1, 2, 6, 21, 23, 44, and 61.

Moreover, according to the present invention, there is provided an HLA-binding peptide binding to an HLA-A type molecule, the HLA-binding peptide containing an amino acid sequence formed by deletion, substitution, or addition of one or two amino acid residues of the amino acid sequence contained in the above-mentioned HLA-binding peptide, and consisting of not less than 8 and not more than 11 amino acid residues.

In this way, the construct containing an amino acid sequence formed by deletion, substitution, or addition of one or a few amino acid residues of a specific amino acid sequence that has the property of binding to an HLA-A type molecule can also exhibit a similar effect to that of the above-mentioned HLA-binding peptide.

Furthermore, according to the present invention, there is provided a DNA segment containing a DNA sequence coding for the above-mentioned HLA-binding peptide.

Furthermore, according to the present invention, there is provided a recombinant vector containing a DNA sequence coding for the above-mentioned HLA-binding peptide.

Furthermore, according to the present invention, there is provided an HLA-binding peptide precursor changing within a mammalian body into the above-mentioned HLA-binding peptide.

Constructs of the present invention are explained above, but any combination of these constructs is also effective as an embodiment of the present invention. Furthermore, conversion of the expression of the present invention into another category is also effective as an embodiment of the present invention.

In accordance with the present invention, since it includes a specific amino acid sequence, an HLA-binding peptide that has excellent properties in binding to an HLA-A type molecule can be obtained.

BRIEF DESCRIPTION OF THE DRAWINGS

The above-mentioned object, other objects, features, and advantages will become more apparent from preferred embodiments explained below by reference to the attached drawing.

FIG. 1 A schematic drawing for explaining an active learning experiment design used in an embodiment.

BEST MODE FOR CARRYING OUT THE INVENTION

Modes for carrying out the present invention are explained below by reference to a drawing. In all the drawings, the same constitutional elements are denoted by the same reference numerals and symbols, so that the explanation will not be repeated.

Embodiment 1

In this embodiment a peptide that contains an amino acid sequence for which the binding to an HLA molecule, predicted by a hypothesis obtained using an active learning experiment method (Japanese Patent Application Laid-open No. H11-316754 (1999)), is 3 or greater in terms of a −log Kd value, and consists of not less than 8 and not more than 11 amino acid residues is used as a candidate for an HLA-binding peptide. As a result of a binding experiment, it has been confirmed that these peptides are actually HLA-binding peptides.

As a result, a large number of HLA-binding peptides that have excellent properties in binding to an HLA-A type molecule because they contain an amino acid sequence for which the binding to the HLA molecule in terms of a −log Kd value is 3 or greater could be obtained efficiently.

Specifically, the HLA-binding peptide related to this embodiment is an HLA-binding peptide that binds to an HLA-A type molecule, contains at least one type of amino acid sequence selected from the group consisting of SEQ ID NOS: 1 to 80, which will be described later, and consists of not less than 8 and not more than 11 amino acid residues.

Among human HLA-A types, about 50% of Japanese people have the HLA-A24 type. Many European and American people, such as German people, have the HLA-A2 type.

All of these sequences herein mentioned are sequences consisting of 9 amino acid residues or 10 amino acid residues contained in gene products of the cancer antigen survivin (GenBank AF077350, BC008718, BC034148, BC065497, HSU75285, AY95969) and its splice variant survivin 2B (GenBank AB028869).

The 9-amino-acid peptide sequences of SEQ ID NOS: 1 to 40 are given in Table 1 and Table 2 below.

TABLE 1

HLA-A24-binding 9 amino acid peptides

| SEQ ID No | 20 Highest Predicted Scores | Predicted Score | SEQ Name | Binding Experiment Data |
|---|---|---|---|---|
| 1 | TLPPAWQPF | 6.7882 | 5 | 8.2648 |
| 2 | AFLSVKKQF | 6.0879 | 108 | 7.7283 |
| 3 | DLAQCFFCF | 5.739 | 53 | |
| 4 | NEPDLAQCF | 5.6903 | 50 | |
| 5 | HRISTFKNW | 5.6859 | 17 | |
| 6 | GAPTLPPAW | 5.5929 | 2 | 6.1588 |
| 7 | SVKKQFEEL | 5.0665 | 111 | |
| 8 | KVRRAIEQL | 5.0567 | 153 | |
| 9 | QCFFCFKEL | 4.9164 | 56 | |
| 10 | ISTFKNWPF | 4.9109 | 19 | |
| 11 | LTLGEFLKL | 4.8292 | 119 | |
| 12 | EELTLGEFL | 4.7307 | 117 | |
| 13 | KKHSSGCAF | 4.7119 | 101 | |
| 14 | LKDHRISTF | 4.7103 | 14 | |
| 15 | LPPAWQPFL | 4.6089 | 6 | |
| 16 | EFLKLDRER | 4.5337 | 123 | |
| 17 | RAIEQLAAM | 4.4903 | 156 | |
| 18 | STFKNWPFL | 4.4592 | 20 | |
| 19 | PFLKDHRIS | 4.4049 | 12 | |
| 20 | EPDLAQCFF | 4.3935 | 51 | |

TABLE 2

HLA-A2-binding 9 amino acid peptides

| SEQ ID No | 20 Highest Predicted Scores | Predicted Score | SEQ Name | Binding Experiment Data |
|---|---|---|---|---|
| 21 | SSGCAFLSV | 4.7757 | 104 | 5.29472 |
| 22 | RMAEAGFIH | 4.5561 | 37 | |
| 23 | TLPPAWQPF | 4.4459 | 5 | 5.3599 |
| 24 | DLAQCFFCF | 4.3216 | 53 | |
| 25 | SVKKQFEEL | 4.3071 | 111 | |
| 26 | TLGEFLKLD | 4.2633 | 120 | |
| 27 | FLEGCACTP | 4.1919 | 27 | |
| 28 | LTLGEFLKL | 4.1361 | 119 | |
| 29 | EFEETAKKV | 4.0951 | 146 | |
| 30 | GAPTLPPAW | 4.0189 | 2 | |
| 31 | FKNWPFLEG | 4.0011 | 22 | |
| 32 | FLKDHRIST | 3.9909 | 13 | |
| 33 | KQFEELTLG | 3.9869 | 114 | |
| 34 | KVRRAIEQL | 3.9465 | 153 | |
| 35 | EELTLGEFL | 3.9308 | 117 | |
| 36 | AFLSVKKQF | 3.9207 | 108 | |
| 37 | LPPAWQPFL | 3.9118 | 6 | |
| 38 | AEAGFIHCP | 3.9017 | 39 | |
| 39 | RAIEQLAAM | 3.8884 | 156 | |
| 40 | NEPDLAQCF | 3.8797 | 50 | |

The 10-amino-acid peptide sequences of SEQ ID NOS: 41 to 80 are given in Table 3 and Table 4 below.

TABLE 3

HLA-A24-binding 10 amino acid peptides

| SEQ ID No | 20 Highest Predicted Scores | Predicted Score | SEQ Name | Binding Experiment Data |
|---|---|---|---|---|
| 41 | TLPPAWQPFL | 6.4239 | 5 | |
| 42 | DHRISTFKNW | 6.0842 | 16 | |
| 43 | NEPDLAQCFF | 6.0416 | 50 | |
| 44 | FLKDHRISTF | 5.9714 | 13 | 7.00797 |
| 45 | RISTFKNWPF | 5.7621 | 18 | |
| 46 | QFEELTLGEF | 5.7396 | 115 | |
| 47 | PTLPPAWQPF | 5.6581 | 4 | |
| 48 | ENEPDLAQCF | 5.6356 | 49 | |
| 49 | AQCFFCFKEL | 5.4317 | 55 | |
| 50 | PDLAQCFFCF | 5.3503 | 52 | |
| 51 | ELTLGEFLKL | 5.2479 | 118 | |

TABLE 3-continued

HLA-A24-binding 10 amino acid peptides

| SEQ ID No | 20 Highest Predicted Scores | Predicted Score | Binding Experiment SEQ Name Data |
|---|---|---|---|
| 52 | HCPTENEPDL | 5.0979 | 45 |
| 53 | HKKHSSGCAF | 5.0665 | 100 |
| 54 | RMAEAGFIHC | 4.9796 | 37 |
| 55 | ISTFKNWPFL | 4.9264 | 19 |
| 56 | MGAPTLPPAW | 4.8622 | 1 |
| 57 | FFCFKELEGW | 4.8526 | 58 |
| 58 | VAYACNTSTL | 4.8355 | 79 |
| 59 | LSVKKQFEEL | 4.8327 | 110 |
| 60 | PFLEGCACTP | 4.7885 | 26 |

TABLE 4

HLA-A2-binding 10 amino acid peptides

| SEQ ID No | 20 Highest Predicted Scores | Predicted Score | Binding Experiment SEQ Name Data |
|---|---|---|---|
| 61 | FLKDHRISTF | 4.9449 | 13  5.5304 |
| 62 | TLPPAWQPFL | 4.7647 | 5 |
| 63 | KEFEETAKKV | 4.5657 | 145 |
| 64 | VAYACNTSTL | 4.5599 | 79 |
| 65 | ELTLGEFLKL | 4.5004 | 118 |
| 66 | LSVKKQFEEL | 4.4975 | 110 |
| 67 | HSSGCAFLSV | 4.4888 | 103 |
| 68 | DDDPIGPGTV | 4.4859 | 70 |
| 69 | STLGGRGGRI | 4.3471 | 86 |
| 70 | TLGEFLKLDR | 4.3276 | 120 |
| 71 | RMAEAGFIHC | 4.2842 | 37 |
| 72 | YACNTSTLGG | 4.2791 | 81 |
| 73 | AQCFFCFKEL | 4.2702 | 55 |
| 74 | MAEAGFIHCP | 4.254 | 38 |
| 75 | FLEGCACTPE | 4.2239 | 27 |
| 76 | DDPIGPGTVA | 4.2078 | 71 |
| 77 | WQPFLKDHRI | 4.1939 | 10 |
| 78 | ELEGWEPDDD | 4.1426 | 63 |
| 79 | FEELTLGEFL | 4.1228 | 116 |
| 80 | AEAGFIHCPT | 4.117 | 39 |

The sequences of SEQ ID NOS: 1 to 40 are sequences consisting of 9 amino acid residues contained in a certain genome protein of the cancer antigen survivin.

The sequences of SEQ ID NOS: 1 to 20 are sequences predicted by the above-mentioned method to be the 20 highest in terms of binding to an HLA-A24 molecule. SEQ ID NOS: 1 to 20 are arranged in decreasing binding order. That is, SEQ ID NO: 1 is the sequence that is predicted to have the best binding. A predicted score for binding to the HLA-A24 molecule and binding experiment data for each sequence are expressed in the form of −log Kd values.

Furthermore, the sequences of SEQ ID NOS: 21 to 40 are sequences predicted by the above-mentioned method to be the 20 highest in terms of binding to an HLA-A2 molecule. SEQ ID NOS: 21 to 40 are arranged in decreasing binding order. That is, SEQ ID NO: 21 is the sequence that is predicted to have the best binding. A predicted score for binding to the HLA-A2 molecule and binding experiment data for each sequence are expressed in the form of −log Kd values.

The sequences of SEQ ID NOS: 41 to 80 are sequences consisting of 10 amino acid residues contained in a certain genome protein of the cancer antigen survivin.

The sequences of SEQ ID NOS: 41 to 60 are sequences predicted by the above-mentioned method to be the 20 highest in terms of binding to an HLA-A24 molecule. SEQ ID NOS: 1 to 20 are arranged in decreasing binding order. That is, SEQ ID NO: 41 is the sequence that is predicted to have the best binding. A predicted score for binding to the HLA-A24 molecule and binding experiment data for each sequence are expressed in the form of −log Kd values.

Furthermore, the sequences of SEQ ID NOS: 61 to 80 are sequences predicted by the above-mentioned method to be the 20 highest in terms of binding to an HLA-A2 molecule. SEQ ID NOS: 61 to 80 are arranged in decreasing binding order. That is, SEQ ID NO: 61 is the sequence that is predicted to have the best binding. A predicted score for binding to the HLA-A2 molecule and binding experiment data for each sequence are expressed in the form of −log Kd values.

Although details are described later, it is clear that there is a correlation between the predicted score and the binding experiment data. That is, although there are slight errors, it can be said that a peptide that is predicted by the above-mentioned method to have high binding to the HLA molecule is found experimentally to have high binding to the HLA molecule.

Since there is no conventional technique for discovering an HLA-binding peptide by utilizing such an experimental design method, there are only a very small number of HLA-binding peptides that have been experimentally confirmed to have HLA-binding properties. Because of this, even when a peptide consisting of 9 amino acid or 10 amino acid residues is randomly synthesized by a conventional method and subjected to an experiment to find out if it binds to an HLA molecule, there is a probability of only about 1 in 100 of finding one that has a binding, in terms of a −log Kd value, exceeding 6.

In accordance with this embodiment, since the technique of finding an HLA-binding peptide by utilizing the experimental design method is used, as described above, as many as 80 sequences of HLA-binding peptides can be found. Furthermore, when the binding of some of the HLA-binding peptides obtained is experimentally examined, it is confirmed that all of the sequences that have been subjected to the experiment exhibit an excellent binding to HLA that is equal to or higher than that predicted.

Among these sequences, an HLA-binding peptide containing at least one type of amino acid sequence selected from the group consisting of SEQ ID NOS: 1, 2, 6, 21, 23, 44, and 61 is experimentally confirmed to bind to a human HLA-A type molecule. It can therefore be said with certainty that it is an HLA-binding peptide that has excellent properties in binding to a human HLA-A type molecule.

The binding to an HLA molecule of the HLA-binding peptide related to the present embodiment is 3 or greater in terms of a −log Kd value, particularly preferably 5 or greater, and more preferably 5.4 or greater.

In the field of biochemistry, it is known that a binding ability, in terms of a −log Kd value, of about 3 is the threshold level for whether or not a peptide actually binds to an MHC. Therefore, if the binding to an HLA molecule, in terms of a −log Kd value, is 3 or greater, it can be said that it is an HLA-binding peptide.

Furthermore, if the binding to an HLA molecule, in terms of a −log Kd value, is 5 or greater, since the peptide obtained has excellent properties in binding to the HLA molecule, it can suitably be used for development of an effective therapeutic drug, preventive drug, and the like for an immune disease and the like.

Moreover, if the binding to an HLA molecule, in terms of a −log Kd value, is 5.4 or greater, the peptide obtained has particularly good properties in binding to the HLA molecule, and it can suitably be used for the development of an even more effective therapeutic drug, prophylactic drug, and the like for an immune disease and the like.

Furthermore, it may be arranged that the HLA-binding peptide related to the present embodiment consists of not less than 8 and not more than 11 amino acid residues.

In this way, if the peptide consists of not less than 8 and not more than 11 amino acid residues, it has excellent properties in binding to an HLA molecule. Furthermore, the cytotoxic T lymphocyte (CTL) specifically recognizes a cancer antigen specific to a cancer cell (CTL epitope) consisting of 8 to 11 amino acids presented in an HLA class I molecule on the surface of a cancer cell, and eliminates the cancer cell by damaging only the cancer cell. It is important to prepare such a CTL epitope consisting of 8 to 11 amino acids that is specific to a cancer cell and the like in order to prepare a vaccine for therapy or prevention against the cancer and the like.

For example, the above-mentioned HLA-binding peptide may be a peptide consisting of amino acid residues alone, but it is not particularly limited thereto. For example, it may be an HLA-binding peptide precursor that is optionally modified with a sugar chain or a fatty acid group and the like as long as the effects of the present invention are not impaired. Such a precursor is subjected to a change involving digestion by a digestive enzyme and the like in a living mammalian body such as in a human digestive organ to become an HLA-binding peptide, thus exhibiting similar effects to those shown by the above-mentioned HLA-binding peptide.

Furthermore, the above-mentioned HLA-binding peptide may be a peptide that binds to a human HLA-A24 molecule.

Furthermore, the above-mentioned HLA-binding peptide may be a peptide that binds to a human HLA-A2 molecule.

In accordance with this constitution, since a peptide is obtained that binds to an HLA-A24 molecule, which is often seen in Asian people, such as Japanese people, it can be utilized in the development of a therapeutic drug, a preventive drug, and the like that is particularly effective for Asian people, such as Japanese people.

Furthermore, in accordance with this constitution, since a peptide is obtained that binds to an HLA-A2 molecule, which is often seen in European and American people in addition to Japanese people, it can be utilized in the development of a therapeutic drug, a preventive drug, and the like that is particularly effective for European and American people in addition to Japanese people.

The amino acid sequence contained in the above-mentioned HLA-binding peptide may be an amino acid sequence derived from cancer antigen survivin protein, but it is not particularly limited thereto. For example, it may be an amino acid sequence derived from an HIV protein, or an amino acid sequence derived from a cedar pollen protein and the like. Moreover, it may contain an amino acid sequence derived from a protein having other pathogenicity or allergenicity.

Embodiment 2

In accordance with this embodiment, there is provided an HLA-binding peptide that binds to an HLA-A type molecule, contains an amino acid sequence formed by deletion, substitution, or addition of one or two amino acid residues of the amino acid sequence contained in the above-mentioned HLA-binding peptide, and consists of not less than 8 and not more than 11 amino acid residues.

As described later, even though the constitution includes an amino acid sequence formed by deletion, substitution, or addition of one or a few amino acid residues of a specific amino acid sequence that binds to an HLA-A type molecule, similar effects to those of the HLA-binding peptide related to the above-mentioned embodiment 1 are exhibited.

That is, it can be predicted that even an amino acid sequence formed by deletion, substitution, or addition of one or two amino acid residues of an amino acid sequence shown in SEQ ID NOS: 1 to 80 that has excellent properties in binding to an HLA-A molecule will show excellent HLA-binding properties in a similar manner.

From another viewpoint, it can be predicted that even an amino acid sequence formed by deletion, substitution, or addition of one or a few amino acid residues of an amino acid sequence predicted by the above-mentioned method to have excellent properties in binding to an HLA-A molecule will show excellent HLA-binding properties in a similar manner. The amino acid residues that are substituted are preferably amino acid residues having similar properties to each other, such as both being hydrophobic amino acid residues.

Moreover, the HLA-binding peptides described in Embodiment 1 and Embodiment 2 can be produced using a method known to a person skilled in the art. For example, they may be artificially synthesized by a solid-phase method or a liquid-phase method. Alternatively, these HLA-binding peptides may be produced by expressing them from a DNA segment or a recombinant vector coding for these HLA-binding peptides. These HLA-binding peptides thus obtained can be identified by a method known to a person skilled in the art. For example, identification is possible by use of Edman degradation, mass spectrometry, and the like.

Embodiment 3

In accordance with the present embodiment, there is provided a DNA segment containing a DNA sequence coding for the above-mentioned HLA-binding peptide. Since the DNA segment related to the present embodiment contains a specific DNA sequence, it can express the above-mentioned HLA-binding peptide.

When the above-mentioned HLA-binding peptide is expressed by using the DNA segment related to the present embodiment, expression may be carried out by incorporating this DNA segment into a cell, or expression may be carried out by using a commercial artificial protein expression kit.

Furthermore, continuous expression may be carried out by incorporating the above-mentioned DNA segment into, for example, a human cell. Because of this, an HLA-binding peptide can be made to be present continuously within a cell by incorporating a DNA segment coding for the HLA-binding peptide into the cell rather than incorporating the HLA-binding peptide itself into the cell. When an HLA-binding peptide is used as a vaccine, such an ability to express continuously is advantageous in terms of enhancing the efficacy of the vaccine.

Moreover, the DNA segment related to the present embodiment can be produced by a method known to a person skilled in the art. For example, it may be artificially synthesized by means of a commercial DNA synthesizer and the like. Alternatively, it may be segmented from the survivin gene by using a restriction enzyme and the like. Alternatively, it may be amplified from the survivin gene by a PCR method using a primer. The DNA segment thus obtained may be identified using a method known to a person skilled in the art. For example, it may be identified by a commercial DNA sequencer.

Embodiment 4

In accordance with the present embodiment, there is provided a recombinant vector that contains a DNA sequence coding for the above-mentioned HLA-binding peptide. Since the recombinant vector related to the present embodiment contains a specific DNA sequence, the above-mentioned HLA-binding peptide can be expressed.

When the above-mentioned HLA-binding peptide is expressed by using the recombinant vector related to the present embodiment, expression may be carried out by incorporating this recombinant vector into a cell, or expression may be carried out by using a commercial artificial protein expression kit.

Furthermore, continuous expression may be carried out by incorporating the above-mentioned recombinant vector into, for example, a human cell. Because of this, the HLA-binding peptide can be made to be present continuously within a cell by incorporating a recombinant vector coding for the HLA-binding peptide into the cell rather than incorporating the HLA-binding peptide itself into the cell. When the HLA-binding peptide is used as a vaccine, such an ability to express continuously is advantageous in terms of enhancing the efficacy of the vaccine.

Furthermore, in the above-mentioned recombinant vector, the amount of HLA-binding peptide expressed can be controlled with high precision by the use of a certain sequence in a regulatory region involved in transcription and expression, such as a promoter region upstream of a DNA sequence coding for the above-mentioned HLA-binding peptide. Moreover, the number of copies of a recombinant vector in a cell can be controlled with high precision by the use of a certain sequence in a regulatory region involved in replication, such as the origin region of the recombinant vector.

Furthermore, the above-mentioned recombinant vector may freely contain a sequence other than the DNA sequence coding for the above-mentioned HLA-binding peptide. For example, it may contain a sequence of a marker gene such as a drug resistance gene.

Moreover, the recombinant vector related to the present embodiment can be produced using a method known to a person skilled in the art. For example, it may be obtained by cleaving a multicloning site of a commercial vector such as pBR322 or pUC19 at a certain restriction enzyme site, and inserting the above-mentioned DNA segment into the site and carrying out ligation. Furthermore, the recombinant vector thus obtained can be identified using a method known to a person skilled in the art. For example, it can be confirmed by agarose gel electrophoresis whether or not the length of the DNA segment cleaved by a predetermined restriction enzyme coincides with the restriction map of a commercial vector such as pBR322 or pUC19 and, furthermore, it can be identified by a DNA sequencer and the like whether or not the above-mentioned DNA sequence is contained in the DNA sequence cut out from the multicloning site.

The constitutions of the present invention are explained above, but any combination of these constitutions is also effective as an embodiment of the present invention. Furthermore, conversion of the expression of the present invention into another category is also effective as an embodiment of the present invention.

For example, in the above-mentioned embodiments, the HLA-binding peptide contains an amino acid sequence derived from a certain genome protein (SEQ ID NO: 81) of the cancer antigen survivin, but an HLA-binding peptide for a pathogen other than survivin, such as an HIV virus, may be employed, and an HLA-binding peptide containing an amino acid sequence derived from a protein, such as a cedar pollen allergen and the like, may be employed.

In this way, if an amino acid sequence that is predicted by the above-mentioned method to have excellent HLA-binding properties is contained, it can be expected that it will exhibit excellent HLA-binding properties in a similar way when confirmation is carried out experimentally. Because of this, these HLA-binding peptides can suitably be used mainly for the therapy or prevention of infectious diseases (influenza, SARS, HIV, HCV and the like), and also for cancer immunotherapy, allergic diseases (pollen allergy (hay fever), rheumatism, atopy, asthma and the like), autoimmune diseases, and the like.

EXAMPLES

The present invention is further explained below by reference to Examples, but the present invention is not limited thereto.

Specifically, procedures of prediction, experiment, and evaluation in the present examples were carried out based on an active learning experiment design, and in general the following steps were repeated. A schematic drawing for the active learning experiment design employed here is shown in FIG. 1.

(1) A trial of a lower-order learning algorithm, which will be described later, was carried out once. That is, a plurality of hypotheses were generated by random sampling from accumulated data and, with regard to randomly expressed candidate query points (peptides), a point that showed the largest distribution of predicted values was selected as a query point to be subjected to an experiment.

(2) The peptide at the selected query point was prepared by a synthesis and purification method, which will be described later, and the actual binding ability was measured by an experiment, which will be described later, and added to accumulated data.

In the present example, as the lower-order learning algorithm, a supervised learning algorithm of a Hidden Markov Model was used, and 20 to 30 types of peptides were predicted and selected per experiment by starting with the initial data for 223 types of peptides; the above-mentioned procedure was repeated four times, and a total of 341 data points were obtained.

More specifically, in the active learning method of the present example, 20 to 30 types of peptides containing an amino acid sequence in which 9 of 20 types of amino acids were arranged were designed and synthesized per experiment. The strength of binding (binding ability) thereof to an HLA molecule was measured. The binding ability (Kd value in molar concentration) was obtained as an experimental result. When the binding ability was high, the peptide was selected as a candidate for an HLA-binding peptide that could be used as a material for a vaccine.

The results thus obtained were inputted into a learning system equipped with a learning machine employing the Hidden Markov Model as a mathematical algorithm, and rules were created. The learning machine sampled different results to prepare the rules. The rules expressed by the learning machine had different constitutions. The rules thus obtained and experimental data were stored as needed as accumulated data.

From among more than $20^9$=500 billion peptide sequences, candidates for a subsequent experiment were selected by the rules, and the above-mentioned process was repeated. In this stage, different rules were applied to experimental candidates, and the candidates for which predictions of the experimental results were divided were subjected to experiment. In this way, since the candidates for which predictions of the experimental results were divided were subjected to subsequent experiment, the final precision of the prediction was increased.

In this way, a plurality of learning machines carried out selective sampling in which samples that would give different predictions were selected as experimental candidates, information could be gained efficiently, and a hypothesis (rule) with high precision could be obtained. Repeating the above-mentioned process four times gave excellent results as in Examples described later. Repeating it seven times or more gave even better results.

In accordance with such an active learning method, the number of repetitions of the binding experiment for peptides consisting of 9 amino acid residues, which would otherwise have to be carried out for the 500 billion or more combinations of all the candidates for HLA-binding peptides, could be reduced. In the active learning method, a rule was formed by experiment, and the experiment was repeated for tens of sequence candidates that were predicted by applying the rule. Because of this, the number of experiments could be cut, and the time and cost of the initial screening could be greatly reduced.

Furthermore, the hit rate for prediction of the binding of a peptide to HLA by the rule obtained by the active learning method reached 70 to 80%, whereas the hit rate by other known techniques such as the anchor method was as low as about 30%.

Synthesis and Purification of Peptide

A peptide was manually synthesized by the Merrifield solid-phase method using Fmoc amino acids. After deprotection, reverse phase HPLC purification was carried out using a C18 column to give a purity of 95% or higher. Identification of the peptide and confirmation of its purity were carried out using a MALDI-TOF mass spectrometer (Voyager DE RP, PerSeptive). Quantitative analysis of the peptide was carried out by a Micro BCA assay (Pierce Corp.) using BSA as a standard protein.

Experiment of Binding Peptide to HLA-A24 Molecule

The ability of a peptide to bind to an HLA-A24 molecule, which is a product of the HLA-A*2402 gene, was measured using C1R-A24 cells expressing the HLA-A24 molecule (cells prepared by Professor Masafumi Takiguchi, Kumamoto University being supplied with permission by Assistant Professor Masaki Yasukawa, Ehime University).

C1R-A24 cells were first exposed to acidic conditions at a pH of 3.3 for 30 seconds, thus dissociating and removing a light chain β2m, which is associated with HLA class I molecules in common, and an endogenous peptide originally bound to the HLA-A*2402 molecule. After neutralization, purified β2m was added to C1R-A24 cells, the obtained product was added to serial dilutions of a peptide, and incubated on ice for 4 hours. Staining was carried out using fluorescently labeled monoclonal antibody 17A12, which recognizes association (MHC-pep) of the three members, that is, HLA-A*2402 molecule, the peptide, and β2m, which had reassociated during the incubation.

Subsequently, the MHC-pep count per C1R-A24 cell (proportional to the strength of fluorescence of the above-mentioned fluorescent antibody) was quantitatively measured using an FACScan fluorescence-activated cell sorter (Becton Dickinson Biosciences). A binding dissociation constant Kd value between the HLA-A24 molecule and the peptide was calculated from the average strength of fluorescence per cell by a published method (Udaka et al., Immunogenetics, 51, 816-828, 2000).

Experiment of Binding Peptide to HLA-A2 Molecule

The ability of a peptide to bind to an HLA-A2 molecule, which is a product of the HLA-A*0201 gene, was measured using strain JY cells expressing the HLA-A*0201.

JY cells were first exposed to acidic conditions at a pH of 3.8 for 30 seconds, thus dissociating and removing a light chain β2m and an endogenous peptide, which were noncovalently associated with the HLA-A*0201 molecule. After neutralization, a reassociation experiment was carried out.

The above-mentioned JY cells and the purified β2m were added to stepped dilutions of peptide for which the binding ability would be measured, and incubation was carried out on ice for 4 hours. HLA-A*0201 molecules that had reassociated up to this point were stained using the associating type specific fluorescently-labeled monoclonal antibody BB7.2.

Subsequently, the amount of fluorescence per cell was measured using a flow cytometer and a dissociation constant Kd value in molar concentration was calculated by a published method (Udaka et al., Immunogenetics, 51, 816-828, 2000).

Evaluation Results

The prediction results and the experimental results shown in Tables 1 to 4 above were obtained.

The sequences of SEQ ID NOS: 1 to 40 in Table 1 and Table 2 are sequences consisting of 9 amino acid residues contained in the full-length sequence of a certain protein of survivin registered in the GenBank.

Furthermore, the sequences of SEQ ID NOS: 1 to 20 are sequences predicted by a hypothesis obtained by the experimental design method explained in Embodiment 1 to be the 20 highest in terms of binding to an HLA-A24 molecule. SEQ ID NOS: 1 to 20 are arranged in decreasing binding order. That is, SEQ ID NO: 1 is the sequence that is predicted to have the best binding.

Furthermore, the sequences of SEQ ID NOS: 21 to 40 are sequences predicted by a hypothesis obtained by the experimental design method explained in Embodiment 1 to be the 20 highest in terms of binding to an HLA-A2 molecule. SEQ ID NOS: 21 to 40 are arranged in decreasing binding order. That is, SEQ ID NO: 21 is the sequence that is predicted to have the best binding.

The full-length amino acid sequence of the certain protein of survivin is shown in SEQ ID NO: 81 (MGAPTLPPAWQP-FLKDHRISTFKNWPFLEGCACTPERMAE-AGFIHCPTENEPD LAQCFFCFKELEGWEPDDDPIG-PGTVAYACNTSTLGGRGGRITREEHKKHSSGC

AFLSVKKQFEELTLGEFLKL-
DRERAKNKIAKETNNKKKEFEETAKKVRRAIEQL
AAMD).

Table 1 and Table 2 each show the amino acid sequences with the 20 highest scores in the predicted results obtained using the above-mentioned prediction program, the predicted score, and the corresponding binding experiment data. All of the binding experiment data were obtained by artificially synthesizing peptide sequences of survivin by the above-mentioned synthetic method.

The sequences of SEQ ID NOS: 41 to 80 in Table 3 and Table 4 are sequences consisting of 10 amino acid residues contained in the full-length sequence of a certain protein of survivin registered in the GenBank.

Furthermore, the sequences of SEQ ID NOS: 41 to 60 are sequences predicted by a hypothesis obtained by the experimental design method explained in Embodiment 1 to be the 20 highest in terms of binding to an HLA-A24 molecule. SEQ ID NOS: 41 to 60 are arranged in decreasing binding order. That is, SEQ ID NO: 41 is the sequence that is predicted to have the best binding.

Furthermore, the sequences of SEQ ID NOS: 61 to 80 are sequences predicted by a hypothesis obtained by the experimental design method explained in Embodiment 1 to be the 20 highest in terms of binding to an HLA-A2 molecule. SEQ ID NOS: 61 to 80 are arranged in decreasing binding order. That is, SEQ ID NO: 61 is the sequence that is predicted to have the best binding.

The full-length amino acid sequence of the certain protein of survivin is shown in SEQ ID NO: 81.

Table 3 and Table 4 each show the amino acid sequences with the 20 highest scores in the predicted results obtained using the above-mentioned prediction program, the predicted score, and the corresponding binding experiment data. All of the binding experiment data were obtained by artificially synthesizing peptide sequences of survivin by the above-mentioned synthetic method.

It can be predicted that any of the peptide sequences formed by substitution of one or two amino acid residues with each other will show excellent binding to an HLA-A molecule. In conclusion, even an amino acid sequence formed by deletion, substitution, or addition of one or a few amino acid residues of an amino acid sequence shown by SEQ ID NOS: 1 to 80 that has excellent properties in binding to an HLA-A molecule can be predicted to similarly show excellent HLA-binding properties.

From another viewpoint, even an amino acid sequence formed by deletion, substitution, or addition of one or a few amino acid residues of an amino acid sequence that has excellent properties in binding to an HLA-A molecule as predicted by the hypothesis obtained by the experimental design method explained in Embodiment 1 similarly can be said to show excellent HLA-binding properties. The amino acid residues that are substituted are preferably amino acid residues that have similar properties to each other, such as the two being hydrophobic amino acid residues.

A group including Udaka, who is one of the inventors, has already reported that even a peptide sequence formed by substitution of one or two amino acid residues in the peptide sequence will similarly show excellent binding properties to an antigen-presenting molecule.

1. "Decrypting the structure of MHC-I restricted CTL epitopes with complex peptide libraries." Keiko Udaka, Karl-Heinz Wiesmuller, Stefan Kienle, Gunter Jung and Peter Walden. J. Exp. Med. 181, 2097-2108 (1995).
2. "Tolerance to amino acid variations in peptides binding to the MHC class I protein H-2Kb." Keiko Udaka, Karl-Heinz Wiesmuller, Stefan Kienle, Gunter Jung and Peter Walden. J. Biol. Chem. 270, 24130-24134 (1995).
3. "Self MHC-restricted peptides recognized by all alloreactive T lymphocyte clone." Keiko Udaka, Karl-Heinz Wiesmuller, Stefan Kienle, Gunter Jung and Peter Walden. J. Immunol. 157, 670-678 (1996).

Therefore, it can be predicted that even the cancer antigen survivin-derived peptide described in the present invention or even the above-mentioned peptide sequence formed by substitution of one or two amino acid residues in the peptide sequence will similarly show excellent binding properties to the HLA-A molecule.

The present invention is explained above by reference to Examples. These Examples are only illustrated as examples, and a person skilled in the art will understand that various modification examples are possible, and such modification examples are included in the scope of the present invention.

The invention claimed is:

1. An isolated HLA-binding peptide comprising the amino acid sequence SEQ ID NO: 21, wherein the peptide is not less than nine and not more than eleven amino acid residues, and said peptide binds to an HLA-A type molecule.

2. The HLA-binding peptide of claim 1, consisting of the amino acid sequence SEQ ID NO: 21.

3. A pharmaceutical composition, comprising the HLA-binding peptide of claim 1 and a pharmaceutically acceptable carrier.

4. A pharmaceutical composition, comprising the HLA-binding peptide of claim 2 and a pharmaceutically acceptable carrier.

* * * * *

SEQUENCE LISTING

```
<160> NUMBER OF SEQ ID NOS: 81

<210> SEQ ID NO 1
<211> LENGTH: 9
<212> TYPE: PRT
<213> ORGANISM: Homo sapiens

<400> SEQUENCE: 1

Thr Leu Pro Pro Ala Trp Gln Pro Phe
1               5

<210> SEQ ID NO 2
<211> LENGTH: 9
<212> TYPE: PRT
<213> ORGANISM: Homo sapiens

<400> SEQUENCE: 2

Ala Phe Leu Ser Val Lys Lys Gln Phe
1               5

<210> SEQ ID NO 3
```

```
<211> LENGTH: 9
<212> TYPE: PRT
<213> ORGANISM: Homo sapiens

<400> SEQUENCE: 3

Asp Leu Ala Gln Cys Phe Phe Cys Phe
1               5

<210> SEQ ID NO 4
<211> LENGTH: 9
<212> TYPE: PRT
<213> ORGANISM: Homo sapiens

<400> SEQUENCE: 4

Asn Glu Pro Asp Leu Ala Gln Cys Phe
1               5

<210> SEQ ID NO 5
<211> LENGTH: 9
<212> TYPE: PRT
<213> ORGANISM: Homo sapiens

<400> SEQUENCE: 5

His Arg Ile Ser Thr Phe Lys Asn Trp
1               5

<210> SEQ ID NO 6
<211> LENGTH: 9
<212> TYPE: PRT
<213> ORGANISM: Homo sapiens

<400> SEQUENCE: 6

Gly Ala Pro Thr Leu Pro Pro Ala Trp
1               5

<210> SEQ ID NO 7
<211> LENGTH: 9
<212> TYPE: PRT
<213> ORGANISM: Homo sapiens

<400> SEQUENCE: 7

Ser Val Lys Lys Gln Phe Glu Glu Leu
1               5

<210> SEQ ID NO 8
<211> LENGTH: 9
<212> TYPE: PRT
<213> ORGANISM: Homo sapiens

<400> SEQUENCE: 8

Lys Val Arg Arg Ala Ile Glu Gln Leu
1               5

<210> SEQ ID NO 9
<211> LENGTH: 9
<212> TYPE: PRT
<213> ORGANISM: Homo sapiens

<400> SEQUENCE: 9

Gln Cys Phe Phe Cys Phe Lys Glu Leu
1               5

<210> SEQ ID NO 10
<211> LENGTH: 9
<212> TYPE: PRT
```

<213> ORGANISM: Homo sapiens

<400> SEQUENCE: 10

Ile Ser Thr Phe Lys Asn Trp Pro Phe
1               5

<210> SEQ ID NO 11
<211> LENGTH: 9
<212> TYPE: PRT
<213> ORGANISM: Homo sapiens

<400> SEQUENCE: 11

Leu Thr Leu Gly Glu Phe Leu Lys Leu
1               5

<210> SEQ ID NO 12
<211> LENGTH: 9
<212> TYPE: PRT
<213> ORGANISM: Homo sapiens

<400> SEQUENCE: 12

Glu Glu Leu Thr Leu Gly Glu Phe Leu
1               5

<210> SEQ ID NO 13
<211> LENGTH: 9
<212> TYPE: PRT
<213> ORGANISM: Homo sapiens

<400> SEQUENCE: 13

Lys Lys His Ser Ser Gly Cys Ala Phe
1               5

<210> SEQ ID NO 14
<211> LENGTH: 9
<212> TYPE: PRT
<213> ORGANISM: Homo sapiens

<400> SEQUENCE: 14

Leu Lys Asp His Arg Ile Ser Thr Phe
1               5

<210> SEQ ID NO 15
<211> LENGTH: 9
<212> TYPE: PRT
<213> ORGANISM: Homo sapiens

<400> SEQUENCE: 15

Leu Pro Pro Ala Trp Gln Pro Phe Leu
1               5

<210> SEQ ID NO 16
<211> LENGTH: 9
<212> TYPE: PRT
<213> ORGANISM: Homo sapiens

<400> SEQUENCE: 16

Glu Phe Leu Lys Leu Asp Arg Glu Arg
1               5

<210> SEQ ID NO 17
<211> LENGTH: 9
<212> TYPE: PRT
<213> ORGANISM: Homo sapiens

```
<400> SEQUENCE: 17

Arg Ala Ile Glu Gln Leu Ala Ala Met
1               5

<210> SEQ ID NO 18
<211> LENGTH: 9
<212> TYPE: PRT
<213> ORGANISM: Homo sapiens

<400> SEQUENCE: 18

Ser Thr Phe Lys Asn Trp Pro Phe Leu
1               5

<210> SEQ ID NO 19
<211> LENGTH: 9
<212> TYPE: PRT
<213> ORGANISM: Homo sapiens

<400> SEQUENCE: 19

Pro Phe Leu Lys Asp His Arg Ile Ser
1               5

<210> SEQ ID NO 20
<211> LENGTH: 9
<212> TYPE: PRT
<213> ORGANISM: Homo sapiens

<400> SEQUENCE: 20

Glu Pro Asp Leu Ala Gln Cys Phe Phe
1               5

<210> SEQ ID NO 21
<211> LENGTH: 9
<212> TYPE: PRT
<213> ORGANISM: Homo sapiens

<400> SEQUENCE: 21

Ser Ser Gly Cys Ala Phe Leu Ser Val
1               5

<210> SEQ ID NO 22
<211> LENGTH: 9
<212> TYPE: PRT
<213> ORGANISM: Homo sapiens

<400> SEQUENCE: 22

Arg Met Ala Glu Ala Gly Phe Ile His
1               5

<210> SEQ ID NO 23
<211> LENGTH: 9
<212> TYPE: PRT
<213> ORGANISM: Homo sapiens

<400> SEQUENCE: 23

Thr Leu Pro Pro Ala Trp Gln Pro Phe
1               5

<210> SEQ ID NO 24
<211> LENGTH: 9
<212> TYPE: PRT
<213> ORGANISM: Homo sapiens

<400> SEQUENCE: 24
```

Asp Leu Ala Gln Cys Phe Phe Cys Phe
1               5

<210> SEQ ID NO 25
<211> LENGTH: 9
<212> TYPE: PRT
<213> ORGANISM: Homo sapiens

<400> SEQUENCE: 25

Ser Val Lys Lys Gln Phe Glu Glu Leu
1               5

<210> SEQ ID NO 26
<211> LENGTH: 9
<212> TYPE: PRT
<213> ORGANISM: Homo sapiens

<400> SEQUENCE: 26

Thr Leu Gly Glu Phe Leu Lys Leu Asp
1               5

<210> SEQ ID NO 27
<211> LENGTH: 9
<212> TYPE: PRT
<213> ORGANISM: Homo sapiens

<400> SEQUENCE: 27

Phe Leu Glu Gly Cys Ala Cys Thr Pro
1               5

<210> SEQ ID NO 28
<211> LENGTH: 9
<212> TYPE: PRT
<213> ORGANISM: Homo sapiens

<400> SEQUENCE: 28

Leu Thr Leu Gly Glu Phe Leu Lys Leu
1               5

<210> SEQ ID NO 29
<211> LENGTH: 9
<212> TYPE: PRT
<213> ORGANISM: Homo sapiens

<400> SEQUENCE: 29

Glu Phe Glu Glu Thr Ala Lys Lys Val
1               5

<210> SEQ ID NO 30
<211> LENGTH: 9
<212> TYPE: PRT
<213> ORGANISM: Homo sapiens

<400> SEQUENCE: 30

Gly Ala Pro Thr Leu Pro Pro Ala Trp
1               5

<210> SEQ ID NO 31
<211> LENGTH: 9
<212> TYPE: PRT
<213> ORGANISM: Homo sapiens

<400> SEQUENCE: 31

Phe Lys Asn Trp Pro Phe Leu Glu Gly
1               5

<210> SEQ ID NO 32
<211> LENGTH: 9
<212> TYPE: PRT
<213> ORGANISM: Homo sapiens

<400> SEQUENCE: 32

Phe Leu Lys Asp His Arg Ile Ser Thr
1               5

<210> SEQ ID NO 33
<211> LENGTH: 9
<212> TYPE: PRT
<213> ORGANISM: Homo sapiens

<400> SEQUENCE: 33

Lys Gln Phe Glu Glu Leu Thr Leu Gly
1               5

<210> SEQ ID NO 34
<211> LENGTH: 9
<212> TYPE: PRT
<213> ORGANISM: Homo sapiens

<400> SEQUENCE: 34

Lys Val Arg Arg Ala Ile Glu Gln Leu
1               5

<210> SEQ ID NO 35
<211> LENGTH: 9
<212> TYPE: PRT
<213> ORGANISM: Homo sapiens

<400> SEQUENCE: 35

Glu Glu Leu Thr Leu Gly Glu Phe Leu
1               5

<210> SEQ ID NO 36
<211> LENGTH: 9
<212> TYPE: PRT
<213> ORGANISM: Homo sapiens

<400> SEQUENCE: 36

Ala Phe Leu Ser Val Lys Lys Gln Phe
1               5

<210> SEQ ID NO 37
<211> LENGTH: 9
<212> TYPE: PRT
<213> ORGANISM: Homo sapiens

<400> SEQUENCE: 37

Leu Pro Pro Ala Trp Gln Pro Phe Leu
1               5

<210> SEQ ID NO 38
<211> LENGTH: 9
<212> TYPE: PRT
<213> ORGANISM: Homo sapiens

<400> SEQUENCE: 38

Ala Glu Ala Gly Phe Ile His Cys Pro
1               5

```
<210> SEQ ID NO 39
<211> LENGTH: 9
<212> TYPE: PRT
<213> ORGANISM: Homo sapiens

<400> SEQUENCE: 39

Arg Ala Ile Glu Gln Leu Ala Ala Met
1               5

<210> SEQ ID NO 40
<211> LENGTH: 9
<212> TYPE: PRT
<213> ORGANISM: Homo sapiens

<400> SEQUENCE: 40

Asn Glu Pro Asp Leu Ala Gln Cys Phe
1               5

<210> SEQ ID NO 41
<211> LENGTH: 10
<212> TYPE: PRT
<213> ORGANISM: Homo sapiens

<400> SEQUENCE: 41

Thr Leu Pro Pro Ala Trp Gln Pro Phe Leu
1               5                   10

<210> SEQ ID NO 42
<211> LENGTH: 10
<212> TYPE: PRT
<213> ORGANISM: Homo sapiens

<400> SEQUENCE: 42

Asp His Arg Ile Ser Thr Phe Lys Asn Trp
1               5                   10

<210> SEQ ID NO 43
<211> LENGTH: 10
<212> TYPE: PRT
<213> ORGANISM: Homo sapiens

<400> SEQUENCE: 43

Asn Glu Pro Asp Leu Ala Gln Cys Phe Phe
1               5                   10

<210> SEQ ID NO 44
<211> LENGTH: 10
<212> TYPE: PRT
<213> ORGANISM: Homo sapiens

<400> SEQUENCE: 44

Phe Leu Lys Asp His Arg Ile Ser Thr Phe
1               5                   10

<210> SEQ ID NO 45
<211> LENGTH: 10
<212> TYPE: PRT
<213> ORGANISM: Homo sapiens

<400> SEQUENCE: 45

Arg Ile Ser Thr Phe Lys Asn Trp Pro Phe
1               5                   10

<210> SEQ ID NO 46
<211> LENGTH: 10
```

<210> SEQ ID NO 46
<211> LENGTH: 10
<212> TYPE: PRT
<213> ORGANISM: Homo sapiens

<400> SEQUENCE: 46

Gln Phe Glu Glu Leu Thr Leu Gly Glu Phe
1               5                   10

<210> SEQ ID NO 47
<211> LENGTH: 10
<212> TYPE: PRT
<213> ORGANISM: Homo sapiens

<400> SEQUENCE: 47

Pro Thr Leu Pro Pro Ala Trp Gln Pro Phe
1               5                   10

<210> SEQ ID NO 48
<211> LENGTH: 10
<212> TYPE: PRT
<213> ORGANISM: Homo sapiens

<400> SEQUENCE: 48

Glu Asn Glu Pro Asp Leu Ala Gln Cys Phe
1               5                   10

<210> SEQ ID NO 49
<211> LENGTH: 10
<212> TYPE: PRT
<213> ORGANISM: Homo sapiens

<400> SEQUENCE: 49

Ala Gln Cys Phe Phe Cys Phe Lys Glu Leu
1               5                   10

<210> SEQ ID NO 50
<211> LENGTH: 10
<212> TYPE: PRT
<213> ORGANISM: Homo sapiens

<400> SEQUENCE: 50

Pro Asp Leu Ala Gln Cys Phe Phe Cys Phe
1               5                   10

<210> SEQ ID NO 51
<211> LENGTH: 10
<212> TYPE: PRT
<213> ORGANISM: Homo sapiens

<400> SEQUENCE: 51

Glu Leu Thr Leu Gly Glu Phe Leu Lys Leu
1               5                   10

<210> SEQ ID NO 52
<211> LENGTH: 10
<212> TYPE: PRT
<213> ORGANISM: Homo sapiens

<400> SEQUENCE: 52

His Cys Pro Thr Glu Asn Glu Pro Asp Leu
1               5                   10

<210> SEQ ID NO 53
<211> LENGTH: 10
<212> TYPE: PRT
<213> ORGANISM: Homo sapiens

<400> SEQUENCE: 53

His Lys Lys His Ser Ser Gly Cys Ala Phe
1               5                   10

<210> SEQ ID NO 54
<211> LENGTH: 10
<212> TYPE: PRT
<213> ORGANISM: Homo sapiens

<400> SEQUENCE: 54

Arg Met Ala Glu Ala Gly Phe Ile His Cys
1               5                   10

<210> SEQ ID NO 55
<211> LENGTH: 10
<212> TYPE: PRT
<213> ORGANISM: Homo sapiens

<400> SEQUENCE: 55

Ile Ser Thr Phe Lys Asn Trp Pro Phe Leu
1               5                   10

<210> SEQ ID NO 56
<211> LENGTH: 10
<212> TYPE: PRT
<213> ORGANISM: Homo sapiens

<400> SEQUENCE: 56

Met Gly Ala Pro Thr Leu Pro Pro Ala Trp
1               5                   10

<210> SEQ ID NO 57
<211> LENGTH: 10
<212> TYPE: PRT
<213> ORGANISM: Homo sapiens

<400> SEQUENCE: 57

Phe Phe Cys Phe Lys Glu Leu Glu Gly Trp
1               5                   10

<210> SEQ ID NO 58
<211> LENGTH: 10
<212> TYPE: PRT
<213> ORGANISM: Homo sapiens

<400> SEQUENCE: 58

Val Ala Tyr Ala Cys Asn Thr Ser Thr Leu
1               5                   10

<210> SEQ ID NO 59
<211> LENGTH: 10
<212> TYPE: PRT
<213> ORGANISM: Homo sapiens

<400> SEQUENCE: 59

Leu Ser Val Lys Lys Gln Phe Glu Glu Leu
1               5                   10

<210> SEQ ID NO 60
<211> LENGTH: 10
<212> TYPE: PRT
<213> ORGANISM: Homo sapiens

<400> SEQUENCE: 60

```
Pro Phe Leu Glu Gly Cys Ala Cys Thr Pro
1               5                   10
```

<210> SEQ ID NO 61
<211> LENGTH: 10
<212> TYPE: PRT
<213> ORGANISM: Homo sapiens

<400> SEQUENCE: 61

```
Phe Leu Lys Asp His Arg Ile Ser Thr Phe
1               5                   10
```

<210> SEQ ID NO 62
<211> LENGTH: 10
<212> TYPE: PRT
<213> ORGANISM: Homo sapiens

<400> SEQUENCE: 62

```
Thr Leu Pro Pro Ala Trp Gln Pro Phe Leu
1               5                   10
```

<210> SEQ ID NO 63
<211> LENGTH: 10
<212> TYPE: PRT
<213> ORGANISM: Homo sapiens

<400> SEQUENCE: 63

```
Lys Glu Phe Glu Glu Thr Ala Lys Lys Val
1               5                   10
```

<210> SEQ ID NO 64
<211> LENGTH: 10
<212> TYPE: PRT
<213> ORGANISM: Homo sapiens

<400> SEQUENCE: 64

```
Val Ala Tyr Ala Cys Asn Thr Ser Thr Leu
1               5                   10
```

<210> SEQ ID NO 65
<211> LENGTH: 10
<212> TYPE: PRT
<213> ORGANISM: Homo sapiens

<400> SEQUENCE: 65

```
Glu Leu Thr Leu Gly Glu Phe Leu Lys Leu
1               5                   10
```

<210> SEQ ID NO 66
<211> LENGTH: 10
<212> TYPE: PRT
<213> ORGANISM: Homo sapiens

<400> SEQUENCE: 66

```
Leu Ser Val Lys Lys Gln Phe Glu Glu Leu
1               5                   10
```

<210> SEQ ID NO 67
<211> LENGTH: 10
<212> TYPE: PRT
<213> ORGANISM: Homo sapiens

<400> SEQUENCE: 67

```
His Ser Ser Gly Cys Ala Phe Leu Ser Val
```

<210> SEQ ID NO 68
<211> LENGTH: 10
<212> TYPE: PRT
<213> ORGANISM: Homo sapiens

<400> SEQUENCE: 68

Asp Asp Asp Pro Ile Gly Pro Gly Thr Val
1               5                   10

<210> SEQ ID NO 69
<211> LENGTH: 10
<212> TYPE: PRT
<213> ORGANISM: Homo sapiens

<400> SEQUENCE: 69

Ser Thr Leu Gly Gly Arg Gly Gly Arg Ile
1               5                   10

<210> SEQ ID NO 70
<211> LENGTH: 10
<212> TYPE: PRT
<213> ORGANISM: Homo sapiens

<400> SEQUENCE: 70

Thr Leu Gly Glu Phe Leu Lys Leu Asp Arg
1               5                   10

<210> SEQ ID NO 71
<211> LENGTH: 10
<212> TYPE: PRT
<213> ORGANISM: Homo sapiens

<400> SEQUENCE: 71

Arg Met Ala Glu Ala Gly Phe Ile His Cys
1               5                   10

<210> SEQ ID NO 72
<211> LENGTH: 10
<212> TYPE: PRT
<213> ORGANISM: Homo sapiens

<400> SEQUENCE: 72

Tyr Ala Cys Asn Thr Ser Thr Leu Gly Gly
1               5                   10

<210> SEQ ID NO 73
<211> LENGTH: 10
<212> TYPE: PRT
<213> ORGANISM: Homo sapiens

<400> SEQUENCE: 73

Ala Gln Cys Phe Phe Cys Phe Lys Glu Leu
1               5                   10

<210> SEQ ID NO 74
<211> LENGTH: 10
<212> TYPE: PRT
<213> ORGANISM: Homo sapiens

<400> SEQUENCE: 74

Met Ala Glu Ala Gly Phe Ile His Cys Pro
1               5                   10

<210> SEQ ID NO 75
<211> LENGTH: 10
<212> TYPE: PRT
<213> ORGANISM: Homo sapiens

<400> SEQUENCE: 75

Phe Leu Glu Gly Cys Ala Cys Thr Pro Glu
1               5                   10

<210> SEQ ID NO 76
<211> LENGTH: 10
<212> TYPE: PRT
<213> ORGANISM: Homo sapiens

<400> SEQUENCE: 76

Asp Asp Pro Ile Gly Pro Gly Thr Val Ala
1               5                   10

<210> SEQ ID NO 77
<211> LENGTH: 10
<212> TYPE: PRT
<213> ORGANISM: Homo sapiens

<400> SEQUENCE: 77

Trp Gln Pro Phe Leu Lys Asp His Arg Ile
1               5                   10

<210> SEQ ID NO 78
<211> LENGTH: 10
<212> TYPE: PRT
<213> ORGANISM: Homo sapiens

<400> SEQUENCE: 78

Glu Leu Glu Gly Trp Glu Pro Asp Asp Asp
1               5                   10

<210> SEQ ID NO 79
<211> LENGTH: 10
<212> TYPE: PRT
<213> ORGANISM: Homo sapiens

<400> SEQUENCE: 79

Phe Glu Glu Leu Thr Leu Gly Glu Phe Leu
1               5                   10

<210> SEQ ID NO 80
<211> LENGTH: 10
<212> TYPE: PRT
<213> ORGANISM: Homo sapiens

<400> SEQUENCE: 80

Ala Glu Ala Gly Phe Ile His Cys Pro Thr
1               5                   10

<210> SEQ ID NO 81
<211> LENGTH: 165
<212> TYPE: PRT
<213> ORGANISM: Homo sapiens

<400> SEQUENCE: 81

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
                20                  25                  30

```
Cys Thr Pro Glu Arg Met Ala Glu Ala Gly Phe Ile His Cys Pro Thr
        35                  40                  45
Glu Asn Glu Pro Asp Leu Ala Gln Cys Phe Phe Cys Phe Lys Glu Leu
    50                  55                  60
Glu Gly Trp Glu Pro Asp Asp Pro Ile Gly Pro Gly Thr Val Ala
65                  70                  75                  80
Tyr Ala Cys Asn Thr Ser Thr Leu Gly Gly Arg Gly Gly Arg Ile Thr
                85                  90                  95
Arg Glu Glu His Lys Lys His Ser Ser Gly Cys Ala Phe Leu Ser Val
                100             105                 110
Lys Lys Gln Phe Glu Glu Leu Thr Leu Gly Glu Phe Leu Lys Leu Asp
            115                 120                 125
Arg Glu Arg Ala Lys Asn Lys Ile Ala Lys Glu Thr Asn Asn Lys Lys
        130                 135                 140
Lys Glu Phe Glu Glu Thr Ala Lys Lys Val Arg Arg Ala Ile Glu Gln
145             150                 155                 160
Leu Ala Ala Met Asp
                165
```